United States Patent [19]
Bishop et al.

[11] Patent Number: 6,090,044
[45] Date of Patent: Jul. 18, 2000

[54] SYSTEM FOR DIAGNOSING MEDICAL CONDITIONS USING A NEURAL NETWORK

[76] Inventors: Jeffrey B. Bishop, 1221 Sheridan Ave., Iowa City, Iowa 52240; Malcolm H. Pope, 1983 Highview Cir., Coralville, Iowa 52241

[21] Appl. No.: 08/988,314

[22] Filed: Dec. 10, 1997

[51] Int. Cl.$^7$ .................................................. A61B 5/00
[52] U.S. Cl. ........................................ 600/300; 128/920
[58] Field of Search ............................ 600/377; 395/22; 364/40, 413.2

[56] References Cited

U.S. PATENT DOCUMENTS 5,862,304   1/1999   Ravdin et al. ............................ 395/22

OTHER PUBLICATIONS

"A Comparison of Neural Network & Other Pattern Recognition Approaches to the Diagnosis of Low Back Disorders," B. Bounds et al., *Neural Networks*, vol. 3, pp. 583–591, 1990.
Article entitled "Use of a Probabilistic Neural Network to Estimate the Risk of Mortality after Cardiac Surgery" by Richard K. Orr, MD, published Apr.–Jun. 1997 issue of Medical Decision Making, pp. 178–185.
Article entitled "An Artificial Neural Network System For Diagnosis Of Acute Myocardial Infarction (AMI) In The Accident And Emergency Department: Evaluation And Comparison With Serum Myoglobin Measurements" by Kennedy et al., published Aug., 1996 issue of Computer Methods and Programs in Biomedicine, pp. 93–103.
Article entitled "Artificial Neural Networks For Early Detection And Diagnosis Of Cancer" by Rogers et al., published Dec., 1993 issue of Cancer Letters, pp. 79–83.
Article entitled "Evolving Neural Networks For Detecting Breast Cancer" by Fogel et al., published May, 1995 issue of Cancer Letters, pp. 49–53.
Article entitled "Prediction Of Nodal Metastasis And Prognosis In Breast Cancer: A Neural Model" by Naguib et al., published 1997 issue Anticancer Research, pp. 2735–2742.
Article entitled "An Artificial Intelligent Diagnostic System On Differential Recognition Of Hematopoietic Cells From Microscopic Images" by Beksac et al., published 1997 issue of Cytometry (Communications In Clinical Cytometry), pp. 145–150.
Article entitled "Coronary Artery Bypass Risk Prediction Using Neural Networks" by Lippmann et al., published 1997 issue of Annals of Thoracic Surgery, pp. 1635–1643.
Article entitled "Using Neural Networks To Automatically Detect Brain Tumours In Mr Images" by Dickson et al., published Feb., 1997 issue of International Journal of Neural Systems, vol. 8, No. 1, pp. 91–99.

*Primary Examiner*—Eric F. Winakur
*Assistant Examiner*—Pamela L. Wingood
*Attorney, Agent, or Firm*—Woodard, Emhardt, Naughton, Moriarty & McNett Patent and Trademark Attorneys

[57] ABSTRACT

A system for diagnosing medical conditions, such as low back pain (LBP), is provided, whereby a neural network is trained by presentation of large amounts of clinical data and diagnostic outcomes. Following training, the system is able to produce the diagnosis from the clinical data. While the present invention may be useful in diagnosing LBP in one embodiment, other applications of the present invention, both in the medical field and in other fields, are also envisioned. This intelligent diagnostic system is less expensive and more accurate than conventional diagnostic methods, and has the unique capability to improve its accuracy over time as more data is analyzed.

4 Claims, 7 Drawing Sheets

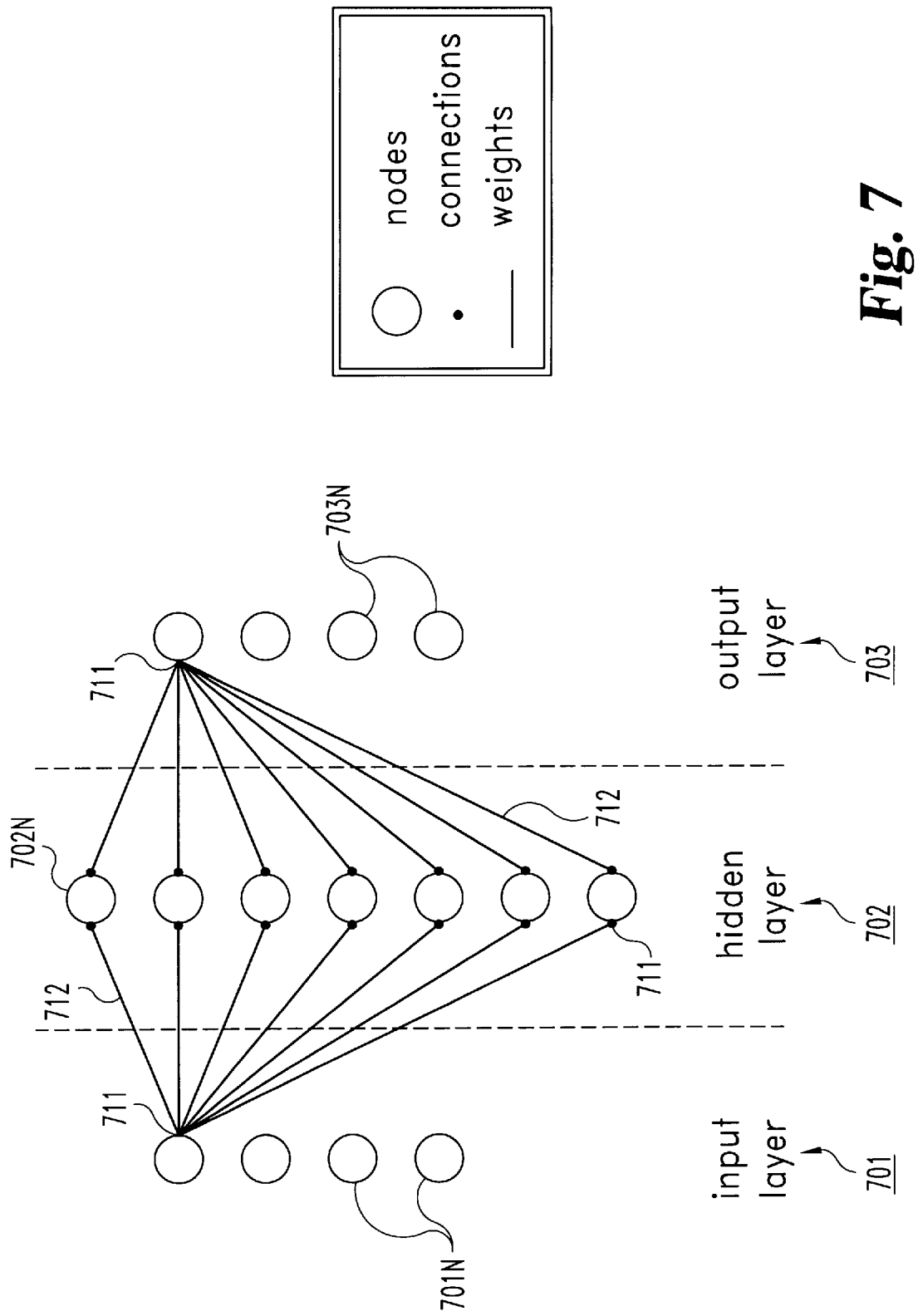

SYSTEM FOR DIAGNOSING MEDICAL CONDITIONS USING A NEURAL NETWORK

BACKGROUND OF THE INVENTION

1. Field of the Invention

The present invention generally relates to a system for diagnosing medical conditions using a neural network trained from clinical data. While the present invention may be adapted for a variety of medical conditions, in one embodiment it may be used for the diagnosis of low back pain.

2. Description of the Prior Art

Low back pain (LBP) is one of the most frequent and most disabling health problems affecting our society, and its incidence appears to be increasing. It has been estimated that, in the United States and Great Britain, this complaint will affect 80% of the population at some point during their lifetime. In Sweden in a 10 year period, 1% of all workdays were lost annually because of low back conditions. The average sickness absence period was 36 days, which is quite similar to the 24 days for the United States and the 33 days for Great Britain. Forty percent of the workers affected with low back pain were disabled for less than one week, while 9.9% were disabled for more than six months. No other disease category was responsible for a greater number of days lost from work. Approximately 2.4 million Americans are disabled because of LBP disorders, the major cause of disability under the age of 45.

Although sophisticated diagnostic means have been developed, it has been estimated that in 80% of cases there is no obvious source of nociception. Furthermore, the relationships between abnormal radiological findings and low back complaints are highly inconsistent. In the wide majority of cases, low back pain is considered as mechanical or functional. Therefore, functional assessment may be considered as useful to investigate those low back troubles. Functional assessment has been used to differentiate between different types of non-specific low back troubles and to prescribe and follow up specific rehabilitation. Differentiate between non-specific back troubles and specific pathologies in basic low back pain screening has also been used before going to more sophisticated and expensive investigation techniques (CT scan, MRI, etc.). In addition many researchers show positive findings in asymptomatic subjects by CT and plain mylography. Degenerate discs, bulging discs and even herniated discs are part of the aging process for the spine and may be irrelevant findings; they are seen on imaging tests of the lumbar spine in a significant percentage of subjects with no history of low back problems. Therefore, abnormal imaging findings seen in a patient with acute low back problems may not be related to that individual's symptoms.

Studies of human spinal motion have dated back to the early 19th century. Kinematic measures are attractive since a kinematic abnormality may reflect underlying pathology. Patients may avoid certain postures that cause pain and muscle activation or coactivation may provide a summary of the trunk neuromuscular status. Hand held devices such as bubble goniometers, pendulum goniometers, inclinometers and so called spondylometers have been used to measure angular differences between points on the back. However, the variability of the measurements is high. Others have made functional assessments, traditionally based on ROM measures or dynamometric measures of strength based on isometric, isokinetic, or isoinertial principles. The principal drawback of recording dynamometric data in this fashion is that successive repetition times are often unequal, thereby prohibiting averaging of repetitions, as well as generating an excessive amount of data. Subsequent interpretation and quantification of trunk dynamometric data is, therefore, often limited to examination of peak and average values of the time-varying data and is, thus, much less clinically relevant since the kinematic movement "patterns" can only be qualitatively (visually) assessed and not truly quantified to allow easy and reproducible comparisons and association with a pathology. Using such information (peak and average values) for diagnostic purposes seems to be of limited value. While lack of strength may be associated with back pain, it gives little information about the underlying diagnosis. While useful and quite easy in population studies, the use of this "quantitative" approach is not easily adaptable to the individual patient. Nevertheless, it may be interesting to assess the efficacy of various treatment modalities for low back pain.

Another drawback to traditional dynametric tests is that maximum effort may not be appropriate for all low back pain patients. Preferred motion generated by physiological submaximal effort is much more comfortable for patients and may reveal details of motion that are masked by higher levels of effort. Preferred motion has been found to be equally consistent to maximum effort low-back movement, and it is possible to predict maximum effort velocities from a knowledge of preferred effort velocities.

An interesting and innovative approach would be to conduct a more "qualitative" study, i.e. one which would examine abnormal movement patterns and profiles and enable their quantification in a reliable fashion. Such research should determine how spinal pathologies modify patterns of motion, and help to identify a "spinal signature" associated with the pathology. The functional based impairment evaluation schemes have traditionally used spinal mobility. Given the poor reliability of range of motion (ROM), its large variability among individuals, and the static psychometric nature of ROM, the use of continuous dynamic profiles of motion with the higher order derivatives has been suggested by others. A marked improvement over the use of ROM has been achieved by preserving information in the continuous profiles. As velocity appears to be a very sensitive variable in low back pain, the study of continuous velocity profiles seems promising. Preliminary studies suggest that certain conditions, such as permanent or transient spinal stenosis or marked bulging disk, are associated with specific movement patterns.

Another drawback of those dynametric measures is that they require heavy and expensive equipment. It has been shown by others that velocity is the most sensitive variable in low back condition, much more sensitive than isometric or dynametric strength. Therefore, it appears that lighter, cheaper equipment measuring displacement and velocity could be sufficient in assessing different patterns of movement associated with different clinical and pathological presentations.

SUMMARY OF THE INVENTION

A system for diagnosing medical conditions, such as low back pain (LBP), is provided, whereby a neural network is trained by presentation of large amounts of clinical data and diagnostic outcomes. Following training, the system is able to produce the diagnosis from the clinical data. While the present invention may be useful in diagnosing LBP in one embodiment, other applications of the present invention, both in the medical field and in other fields, are also envisioned. This intelligent diagnostic system is less expensive and more accurate than conventional diagnostic methods, and has the unique capability to improve its accuracy over time as more data is analyzed.

BRIEF DESCRIPTION OF THE DRAWINGS

FIG. 7 illustrates a sample backpropogation neural network that may be used with the present invention.

DETAILED DESCRIPTION OF THE INVENTION

Figure 1:
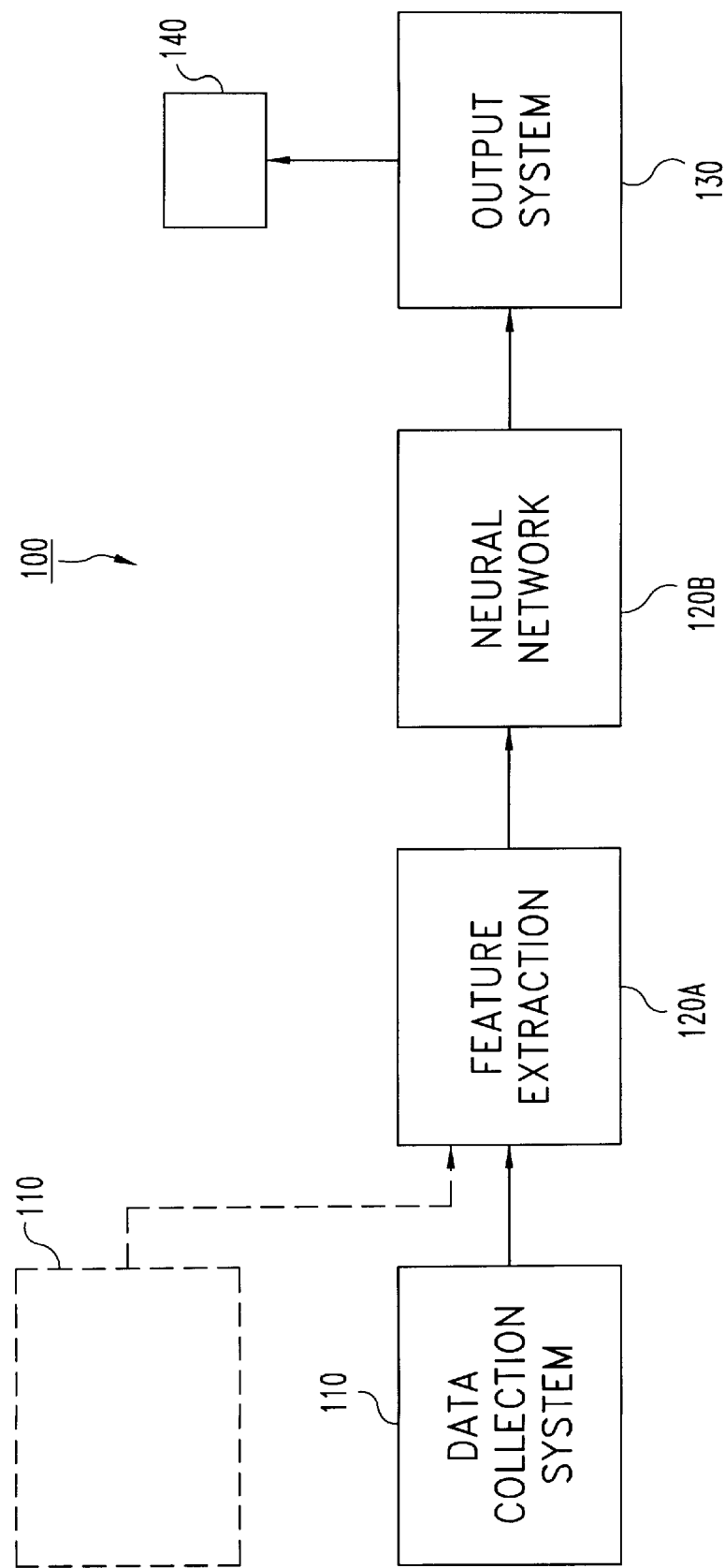
FIG. 1 depicts an overall block diagram of the present invention, in one embodiment.

Classification of low back pain (LBP) has been the subject of many studies. One of the most elaborate and accomplished works in this field was that of the Quebec Task Force (QTF) which distinguished 12 categories based on history, complaints, clinical exam, and complementary examinations such as EMG, MRI, etc. The QTF categories are useful because they allow patients to be classified based on information that is available in the clinical setting.

Numerous studies have also been reported that have failed to show differences between LBP and normal subjects. For example, discriminant analysis has been used to classify LBP as a function of ROM, isometric extension strength, and spectral electromyography. Sensitivity has been found to be 66% and specificity was 71%. Others have used various measures of isometric as well as dynamic strength to distinguish between normal and LBP subjects. These measures also resulted in poor specificity and sensitivity measures.

Rather than using information that is subjective (patient complaints) or expensive to obtain (imaging, clinical exams) to classify patients, the present invention introduces a neural network system that can use objective and readily available information—e.g., the patient's pattern of motion in a simple protocol—to effectively classify patients with respect to back condition. The motion data can be collected with inexpensive equipment that can be used with a wide range of patients and for a variety of rehabilitation purposes, for example pre- and post-rehabilitation evaluation.

As used in the present invention, neural networks are a processing technique capable of learning complex, nonlinear relationships between inputs and outputs during exposure to input patterns and desired output patterns. In this case, the inputs consist of features of motion and the desired output is the pain classification of the patient. A neural network consists of a network of simple processing units connected together to perform data processing tasks. The structure of the neural network is somewhat analogous to the structure of biological neural networks in the brain. When a neural network is presented with an input data pattern, it produces an output pattern. A neural network is trained for a specific processing task by presentation of large amounts of data. The neural network modifies its structure by changing the strength of communication between processing units (called neurons) to improve its performance on the training data.

Following training, the neural network is able to generalize to provide solutions to novel input patterns, provided that the training data was adequate. Neural networks are typically used for applications with a large number of inputs, noisy or variable input data, or non-linear relationships between variables. For example, neural networks have been used successfully in applications such as speech recognition, handwriting recognition, and ECG analysis, which involve pattern matching of noisy and variable input data to a template pattern. Neural nets have even been used to determine the total cost of a worker's compensation claim based on medical and demographic indicators.

The present invention comprises a computer-based system for intelligent diagnosis of medical conditions, such as low back pain (LBP), using artificial neural networks. Referring to FIG. 1, in one embodiment the present system 100 may include a data collection system 110 to be used, for example, at medical clinics to collect data regarding a particular medical condition, a diagnostic and data analysis system 120 which may comprise a feature extraction function and a neural network trained to make a particular type of medical diagnosis, and a output system 130 for generating and delivering a diagnostic report to, for example, the clinic. The neural network 120B for diagnosis may be at a remote location from the clinical sites.

In one embodiment, the data collection system 110, the diagnostic and data analysis system 120 and the output system 130 may comprise various components as described below. For example, the data collection system 110 may comprise instrumentation to collect data from patients to be used for diagnosis. This could include back movement measurements, as in the case of low back pain diagnosis, or other clinical information for other types of diagnosis. The data collection system 110 could also collect observations and other notes from the clinician and results from routine clinical examination. The data may be stored in electronic form for processing, such as on a storage media 111 (e.g., a hard disk, etc.).

The diagnostic and data analysis system 120 may comprise (1) a feature extraction component 120A and (2) a diagnostic unit 120B based on, for example, neural networks. The feature extraction component 120A may not be required for some types of data. The feature extraction component 120A processes the data to extract the most relevant features for diagnosis. In the case of low back pain diagnosis from motion data, the feature extraction component 120A may find features including shape, velocity, and symmetry features from the data. The features to be extracted to make a diagnosis may be determined in consultation with experts in that clinical field and also by statistical analysis to determine which features are more likely to be useful for diagnosis by the neural network 120B.

The neural network diagnostic component 120B may comprise one or more neural networks. The input to the neural network 120B may be the set of features, and the output a diagnosis of disease, or a recommendation for further diagnostic tests. The diagnostic data analysis stage 120 may be, for example, implemented on an Intel-based personal computer (PC), or a larger computer. The neural networks 120B may be implemented using a development system such as MATLAB from Mathworks (Natick, Mass.) or can be developed in a computer language such as C from conventional algorithms and processes.

The output system 130 may produce a printed diagnostic report, a FAX in electronic form via a modem, or a report delivered in electronic format via e-mail, the world wide web (WWW) or other computer network. The report may contain the diagnostic output from the system 120 and may also contain other information such as suggestions for additional diagnostic tests, or information for the patient about his/her medical condition. Again, the output system 130 may be implemented on a standard PC, or equivalent.

1. Data Collection System 110

Data regarding low back pain (LBP) may of course be manually collected from patients using the Quebec Task Force (QTF) classification criteria, or equivalent. For example, a QTF pain classification of zero (0) indicates no low back pain, and a nonzero QTF pain classification indicates low back pain is present, with higher pain numbered classifications generally indicating more serious pain conditions. Such manually collected data, also including findings during routine clinical examination, may be used to train the neural network 120B, along with data collected through more automatic means using certain equipment, as described in further detail below.

For purposes of providing addition data to train the neural network 120B, back motion may be measured using a protocol that includes flexion/extension (7 repetitions), lateral bending (7 repetitions), axial rotation (7 repetitions), clockwise circumduction (4 repetitions), and counterclockwise circumduction (4 repetitions) movement tests. Subjects may be given standardized instructions on how to perform the movements and may be allowed to practice prior to measurement. The subjects may be instructed to perform movements as far as is comfortable at their preferred pace.

Figure 2:
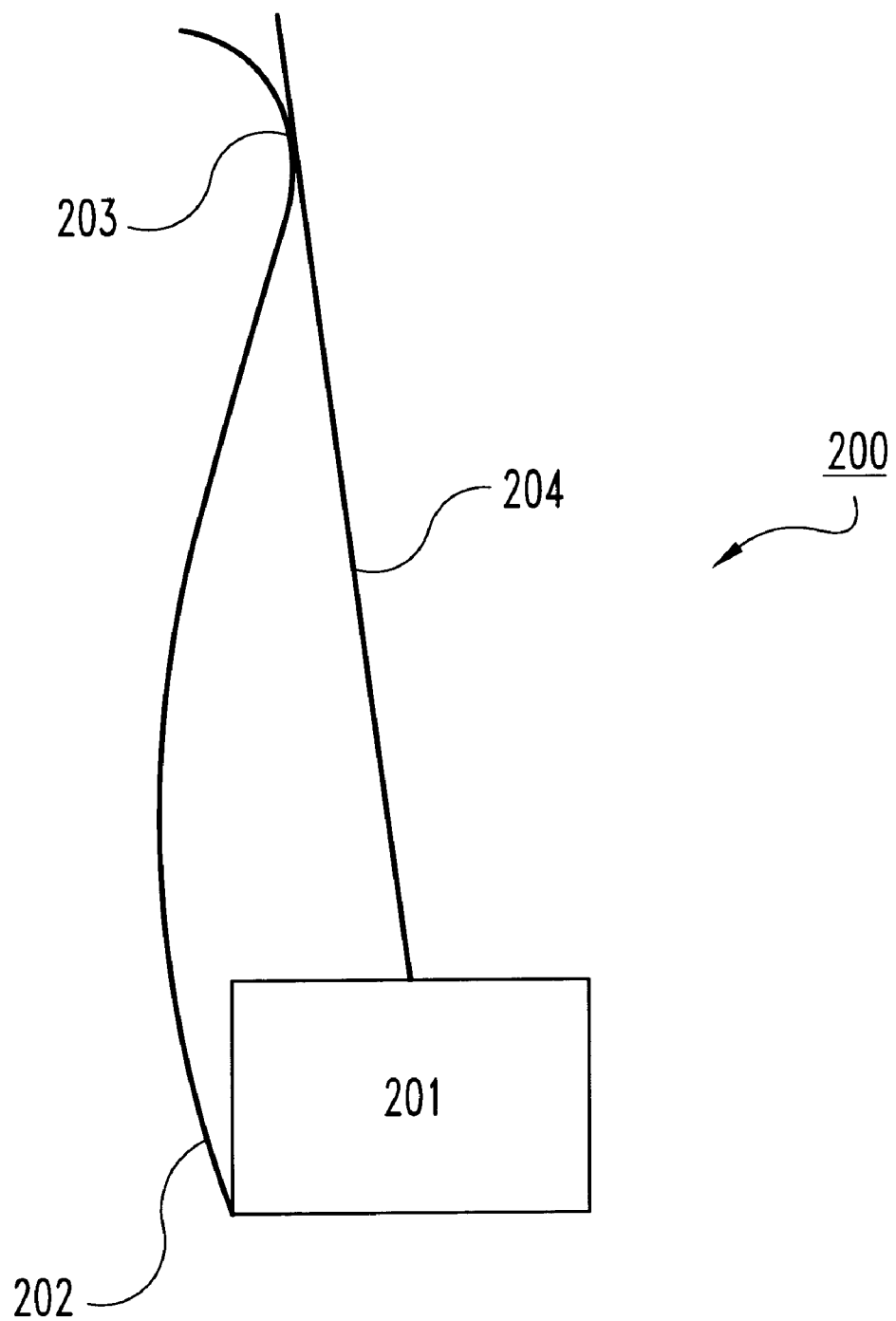
FIG. 2 is a schematic diagram of a triaxial goniometer that may be used in conjunction with the present invention.

In a preferred embodiment, a triaxial goniometer may be used as a data collection system 110 to measure the motion of the lumbar spine at 100 Hz. One, the B-Tracker™ system (Isotechnologies, Hillsborough, N.C.), a triaxial goniometer, may be used for this purpose. FIG. 2 illustrates the main components of such a triaxial goniometer.

Referring to FIG. 2, the triaxial goniometer 200 uses potentiometers for transduction of bending angle to an electrical voltage that is digitized and stored for analysis. The potentiometers are arranged in a mechanical system so that flexion-extension bending, lateral bending, and rotational bending are measured as the subject wearing the instrument moves about. A process based on, for example, a mathematical model, is used to adjust for the distance of the goniometer 200 from the subject's spine, so that the output is a measurement of movement of the back itself, rather than the movement of the instrument.

Referring to FIG. 2, reference numeral 201 is the transduction unit that contains the potentiometers. Reference numeral 202 depicts the subject's low back, where the transduction unit 201 is attached, typically with a belt. Reference numeral 203 indicates an area of the subjects upper back, typically near the shoulder blades. A belt is worn at this level, and a rod or bar (204) is attached at that point. As the subject moves his/her back, the bar 204 moves. This causes the linkage inside the transduction unit 201 to move and the readings of the potentiometers inside indicate the angle of bending of the subject's spine.

When a subject uses the triaxial goniometer 200, channels for flexion/extension, lateral bending, and rotation may be recorded. The position of the back vs. time may be digitized and stored either in the memory of the triaxial goniometer 200 for later upload to a computer, or may be stored directly on a computer via a cable (not specifically shown). The computer used to store these measurements may be part of the data collection system 110.

Figure 3:
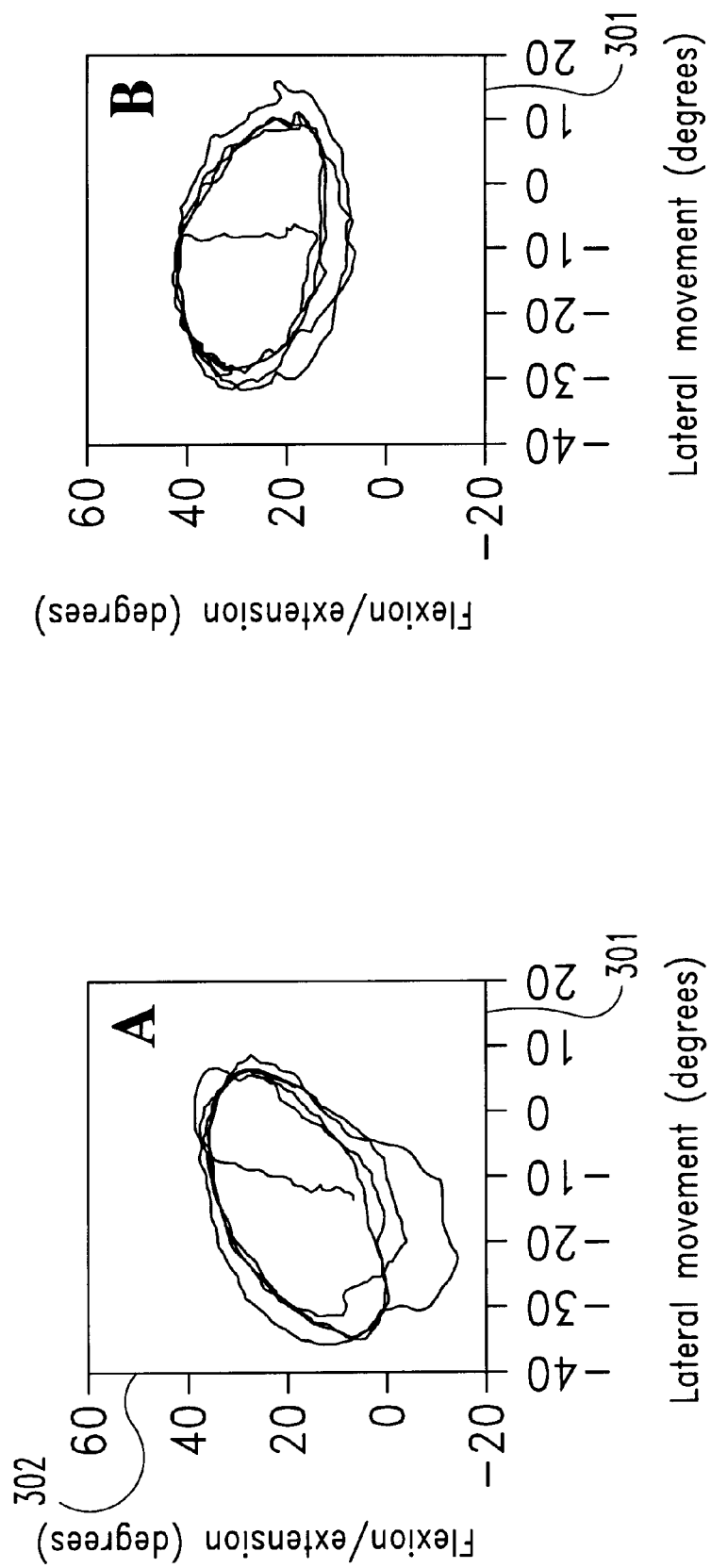
FIGS. 3A, 3B, 4A and 4B are sample circumduction graphs plotted using data collected by the triaxial goniometer of FIG. 2.

FIGS. 3A and 3B show typical circumduction movement plotted from clinical data for clockwise and counterclockwise movement respectively, where axes 301 corresponds to lateral movement (degrees), and axes 302 corresponds to flexion/extension (degrees). During circumduction, the subject bends the low back in a pattern such that the subject's head moves in an approximately elliptical pattern when viewed from above.

Several types of features may be extracted from the movement data for analysis by the neural network 120B, including velocity, shape, and symmetry features. Previous research by others has suggested the importance of velocity changes in low back pain, and so the average and maximum values of flexion/extension, lateral, and rotational velocities during movement tests may be computed. Parameters defining the shape and range of motion may also be used, including positions of maximal flexion, extension, lateral bending, and rotational bending during dynamic motion and time of occurrence of these maximal positions relative to other key events in the movement. The symmetry of the shape of the movement, in terms of the maximal displacement in each direction of motion, as well as the symmetry of the velocity of the movement may be evaluated. The symmetry of the velocity of each movement may be evaluated by measuring the amount of time spent moving in each direction of flexion, extension, and lateral bending. For example, a subject could spend 60% of the time during the protocol moving in lateral bending to the left and 40% moving to the right, which would indicate that the movement was asymmetric with respect to velocity in the lateral direction.

Figure 4:
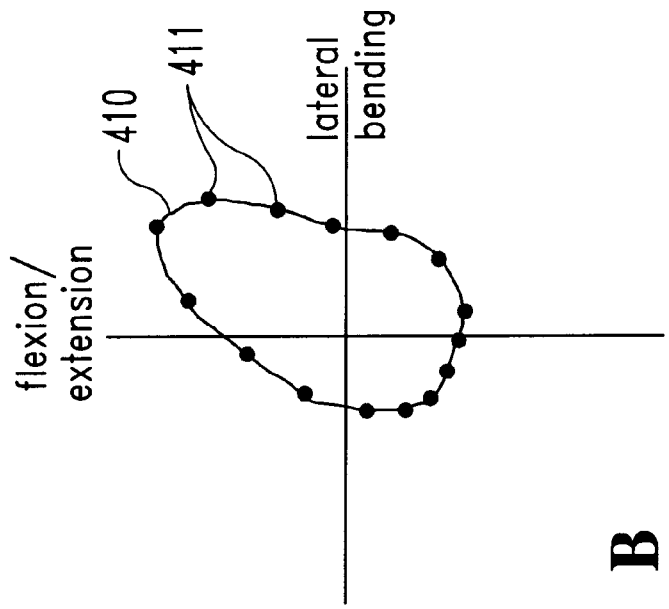
Figure 4:
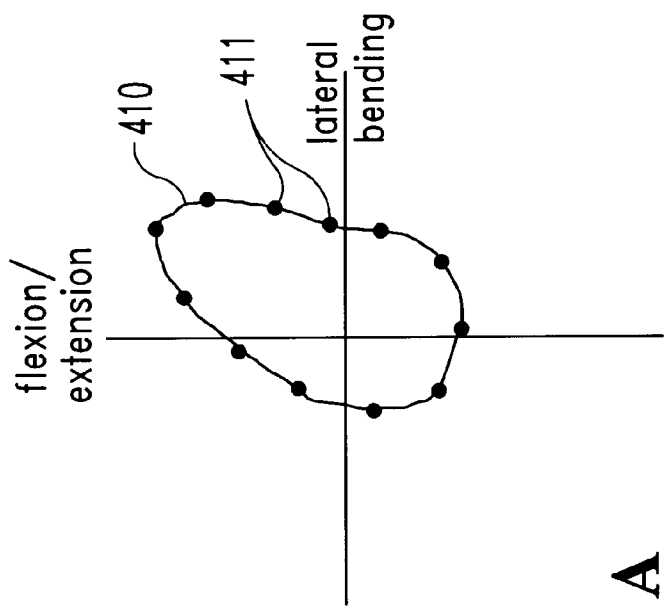

In FIGS. 4A and 4B, the curves 410 represent a clockwise circumduction shape, and the dots 411 represent measurement at uniform time intervals. Although the shapes of the curves 410 in FIGS. 4A and 4B are the same, the velocity characteristics are different. In FIG. 4A, the movement is uniform in velocity, and in FIG. 4B, the subject slows down for part of the movement. The movement in FIG. 4B is asymmetric with respect to velocity, with a larger proportion of time spent moving in the negative lateral direction than in the positive lateral direction.

For a given type of diagnosis, the data may be collected from a number of remote clinical sites via multiple systems 110 and sent to a central site for processing by the neural network 120B. This would provide the advantage of allowing the neural network's 120B performance to improve by being exposed to a larger amount of data. In this case, a data collection system 110 would be implemented at each clinical site, and the analysis system 120 would be implemented at a central site. The diagnostic report generated by the output system 130 would typically be delivered back to the site, of data collection (110).

The data may be collected by system 110 using appropriate clinical instruments and stored in digital form on a computer hard disk, floppy disk, CD-ROM, or other digital storage medium 111. This data may be transmitted to the analysis system 120 for processing using a phone line or computer connection using standard communication protocols.

2. Diagnostic and Data Analysis System 120

Figure 5:
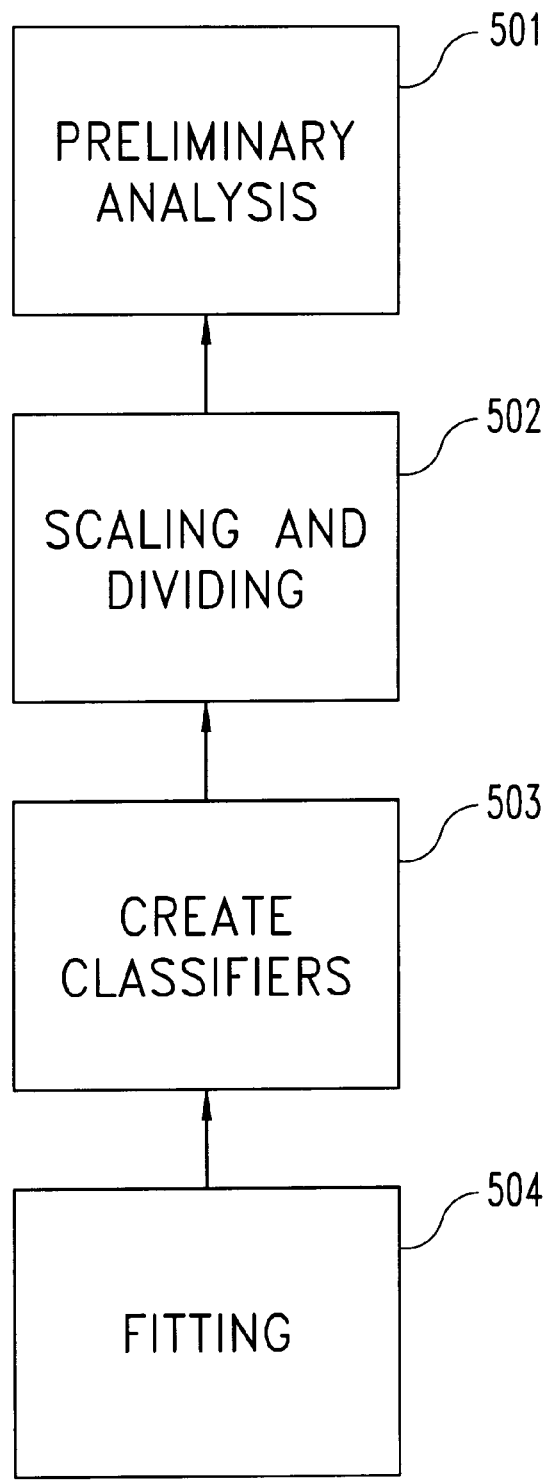
FIG. 5 is a process diagram illustrating a process that may be performed by the present invention.

The diagnostic and data analysis system 120 is described in detail below with respect to the flow diagram of FIG. 5.

In step 501, a preliminary analysis may be performed to determine the separability of low back pain (LBP) groups based on motion data using the neural network of the diagnostic and data analysis system 120 (the neural network 120B is described in further detail with respect to FIG. 7). In one embodiment, motion features may be extracted from data collected during 5 motion tests (flexion/extension, lateral bending, rotational bending, clockwise circumduction, and counterclockwise circumduction) for each subject. A radial basis function network with 30 clusters may be used to classify the data. Radial basis function networks use a set of gaussian activation functions to pave the input space with a set of receptive fields. The mean (position) and standard deviation (width) of the gaussian functions are adapted during training to minimize output error and thus achieve the best classification accuracy. Based on the success of the preliminary analysis, further studies may be performed.

In step 502, the motion features that are extracted in step 501 may be scaled using sigma scaling, and divided into training and test (validation) sets. The data in the validation set may have the same mean and standard deviation as the training set to enable a fair comparison of the performance. The data in the test set may be withheld from analysis until after training is complete to simulate testing new patients.

In step 503, two separate classifiers may be created. The first distinguishes between patterns associated with LBP versus no LBP, and the second distinguishes between classifications of LBP once the presence of LBP is indicated by the first classifier (see FIG. 6).

Figure 6:
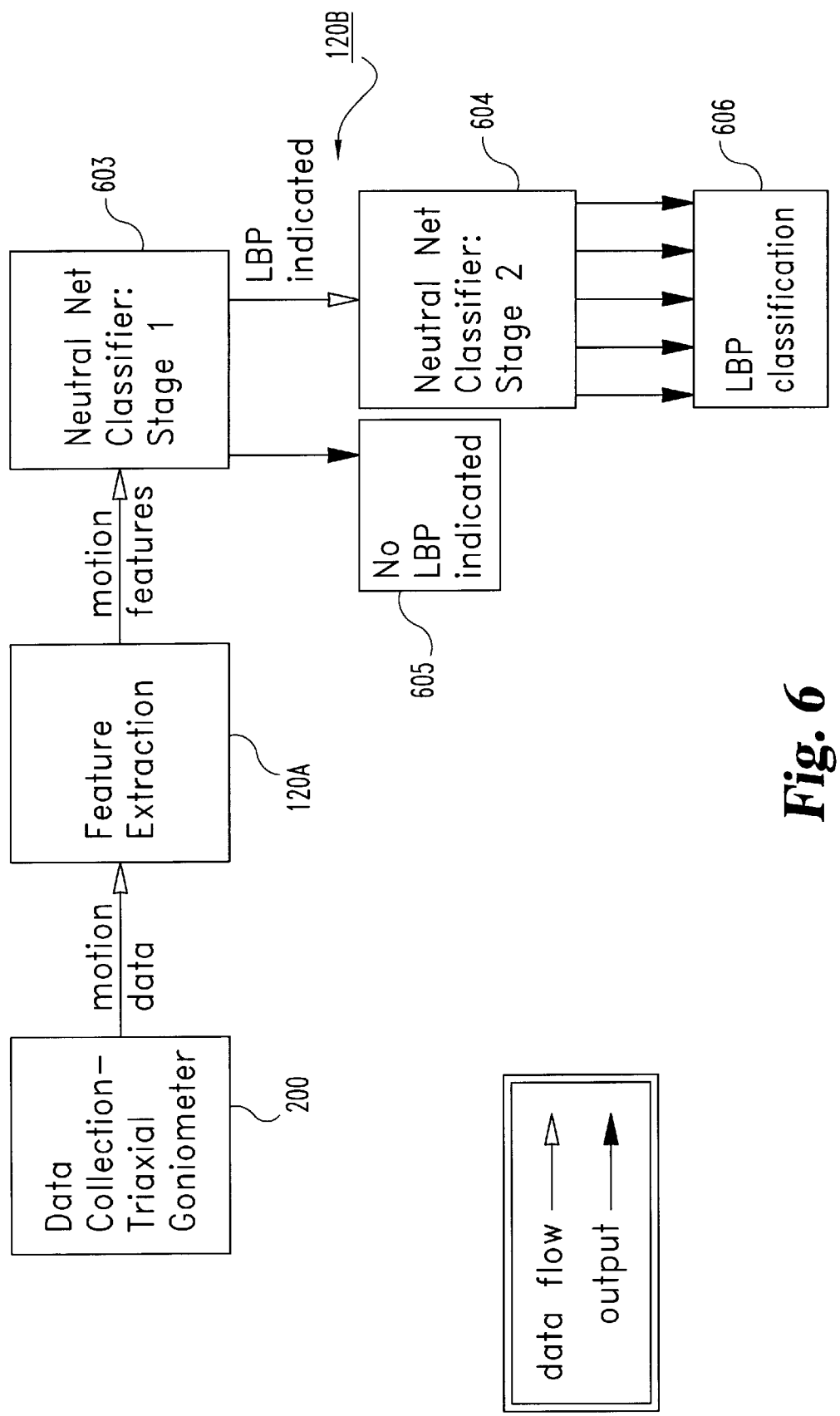
FIG. 6 is an alternate block diagram depicting the present invention.

FIG. 6 shows a block diagram of a system that has been implemented for classification of low back pain. Data is collected using a triazial goniometer 200. Features of the motion data such as velocity, shape, and symmetry features are extracted from the data in 120A. This set of features is input to the first stage 603 of the neural network classifier which is trained to produce an output to indicate whether the subject does or does not have low back pain. If the first stage 603 indicated that the subject has no low back pain, this is the final output 605. If low back pain is indicated, the second stage classifier 604, which has been previously trained, produces an output to indicate which classification of back pain, as indicated in 606.

Training and test sets may be created for the first classifier using the entire pool of subjects and for the second classifier using subjects with non-zero QTF classification. Since the second classifier is concerned only with determining the LBP classification, the cases with QTF=0 (no LBP) are not during training or testing.

For the analysis, groups of QTF classification categories may be used so that more patients will be in each group for analysis. The QTF classifications fall into the following groups: subjective complaints (QTF categories 1–4) objective signs (QTF categories 5–7), post-operative (QTF categories 8, 9.1, 9.2), and non-specific LBP (QTF category 10). A further distinction in the analysis may be made between subjective complaint without pain radiation (QTF category 1) and subjective complaint with pain radiation (QTF categories 2–4). In one embodiment, the classification of 11 ('all other diagnoses') may not be used in the analysis because of the potential for large variations among these patients.

In step 504, four types of models may be used to fit the motion feature data with the pain classification for each subject: linear regression, multiple adaptive regression splines (MARS), RPROP neural networks, and radial basis function neural networks. The linear model (linear regression) may be used initially for comparison with non-linear methods. MARS is a nonlinear fitting method that uses a selected number of splines to fit the data. The shape of the splines is adapted recursively to obtain the best classification results. RPROP is an enhancement of the backpropagation neural network architecture that learns during training using the error at the output to update the weights throughout the network to minimize the output error. FIG. 7 shows a conceptual diagram of a neural network 120B, comprising an input layer 701 with corresponding nodes 701N, a hidden layer 702 with corresponding nodes 702N and an output layer 703 and corresponding nodes 703N. Connections 711 are also denoted in FIG. 7, as are weights 712 between each node.

The radial basis function neural network uses a set of gaussian activation functions to the input space with a set of receptive fields. The mean (position) and standard deviation (width) of the gaussian functions are adapted during training to minimize output error and thus achieve the best classification accuracy.

3. The Output System 130

The analysis system 120 presents its diagnostic result to the output system 130. The output system 130 may generate a diagnostic report indicating the diagnostic result, and may contain other information such as a recommendation for subsequent clinical tests or information for the patient on his/her medical condition. The output system 130 may deliver the report directly to the clinical customer using FAX, e-mail, world wide web (WWW, or other electronic transmission; or may submit a printed report via surface mail delivery. Alternatively, the output system 130 may generate a signal to an external device 140 for further processing. For example, device 140 may comprise a computer system for automatically prescribing treatment of the medical condition, etc.

The features extracted from the motion data, previously described, are useful in distinguishing LBP condition. Subjects with LBP show decreased maximum range of motion in flexion/extension, lateral bending, and rotation compared to subjects without LBP. These differences are statistically significant based on F-tests with nominal a set at 0.05, except for the flexion test (a<0.15). The differences in average velocity (absolute value) between subjects with and without LBP are statistically significant using t-tests assuming unequal variances with a set at 0.05.

For the preliminary analysis, the output of the radial basis function classifier may be analyzed under 3 conditions. In Case I, the model is able to correctly distinguish between LBP (non-zero QTF pain classification) and no LBP (zero QTF pain classification) with at least an 86% degree of accuracy. In Case II, the predicted and actual Quebec Task Force pain classifications may be divided into 4 pain classes- QTF pain classifications of 0, 14 and 10, 5–7, and 8–9.2. With these 4 pain classes, the model has been shown to be correct with a degree of accuracy of 72%. In Case III, the predicted and actual Quebec Task Force pain classifications are divided into 6 classes, with QTF pain classification groups of 0, 1, 2–4, 5–7, 8–9.2, and 10. With these 6 pain classes, the model has been shown to be correct with a degree of accuracy of 65% accuracy.

The results of the analysis models justify the need for a nonlinear fit to obtain good classification results for this problem. The nonlinear model provides a better representation of the data, and therefore is a better predictor than a linear model.

Passing the test data from non-zero QTF classification patients through the Stage 1 classifier resulted in a 72% success in the correct prediction of the non-zero QTF classification. Many of the cases that failed showed a borderline zero QTF prediction, and thus may be improved with an increase in the size of the data set and additional feature extraction from the motion data.

In sum, good discrimination of low back pain (LBP) can be achieved by classifying with a simple and inexpensive device, such as the B-Tracker™ triaxial goniometer of FIG. 2. The data collection 110 and neural network classification system 120 may be implemented on a low-cost PC such as an Intel-based personal computer, which allows on-site processing using a simple interface to guide the process. The clinician may do a basic screening with the system and determine which patients may need more expensive investigation and which could undergo immediate rehabilitation for mechanical low back pain. It can thus be determined which patients should get investigations such as MRI, or be referred to physical therapy. The technique will also enable clinicians to follow up with patients to assess progress or the evolution of active conservative treatment. Thus, the present system could save unnecessary imaging exams which are too often prescribed for low back pain. In the future more data may be obtained to enable better training of the non-linear models, particularly for the non-zero QTF classifications. The capability of classifying specific low back pain pathologies may be developed.

It is important to note that it is possible that an incorrect QTF classification may be made by the clinician and then used to train the neural network classification system 120. As discussed previously, neural networks are relatively tolerant of noisy data, and infrequent errors in the training data would have only a small effect on the overall classification accuracy since large amounts of data are used. However consistent QTF misclassification in the training data could lead to misclassification by the neural network 120B.

Also, in the previous discussion, the test set may be selected randomly from the entire data set, with proportionate distribution of QTF classifications. In one embodiment, the data in the test set is not used for training the neural network 120B, and thus is presented as novel data. Since the training and test data sets may contain data collected from different clinical sites, it is expected that the classification system would be able to generalize successfully to data collected by other clinicians using the same methods.

It has therefore been demonstrated the usefulness of neural networks in classification of LBP. The technique will may provide highly valuable assistance to classify patients. A novel feature of the present invention is that the neural network system 120 learns and improves accuracy with use and feedback. Each physician or user can use and apply the techniques taught herein to other classification applications as well. For example, the teachings of the present invention may be applied to other medical fields, including diagnosis of Alzheimer's disease, urinary incontinence, pressure ulcers, cataract, benign prostatic hyperplasia, unstable angina, heart failure, otitis media with effusion. These have been identified as focus areas by the Agency for Health Care Policy and Research in an effort to improve the quality of health care, reduce its cost, and broaden access to essential services. Other uses include occupational medicine, sports science, etc., and even to other non-medical uses. This intelligent system would have potential applications in telemedicine, home health care, and outpatient clinics. Additionally, the present invention may be applied to LBP in other ways, such as a classification system for LBP based on dynamic motion features, with classifications made based on nonlinear groupings of patients with similar motion characteristics. In any event, the techniques of the present invention show much better accuracy than previous techniques, with a simpler protocol and more flexible possibility of evolution because of the learning inherent in neural networks.

The teachings of the present invention also confirms that continuous patterns of movement can be modified by different pathologies in a specific way, while showing the influence of pathology on the trunk kinematics. The importance of trunk velocity as a marker of LBP and a highly sensitive variable of low back troubles is also confirmed.

The present invention may also be applied for sub-classifying patients presenting with non-specific low back pain (QTF=10). Those patients are those who probably benefit the most from an active rehabilitation program. By sub-classifying this group, it is possible to apply more specific physical therapy and rehabilitation modalities and thus make treatment more efficient. In addition, the efficiency should result in a more rapid return to work, the best treatment for most LBP.

Although the present invention has been described with particular reference to certain preferred embodiments thereof, variations and modifications of the present invention can be effected within the spirit and scope of the following claims.

What is claimed is:

1. A system for diagnosing an unknown low back pain condition, comprising:
   A. means for generating a plurality of training data sets, each training data set including measurements of flexion-extension bending, lateral bending, and rotational bending associated with an historical occurrence of the low back pain condition, and a known diagnosis value associated with the historical occurrence of the low back pain condition;
   B. a neural network;
   C. means for training the neural network using the plurality of training data sets; and
   D. means, responsive to the trained neural network, for generating a target diagnosis value based upon selected measurements of flexion-extension bending, lateral bending, and rotational bending for an unknown low back pain condition.

2. The system of claim 1, wherein the training data sets generating means comprises a triaxial goniometer.

3. The system of claim 1, further comprising:
   (e) means for receiving the target diagnosis value and for prescribing appropriate treatment of the low back pain condition.

4. A process for diagnosing an unknown low back pain condition using a neural network, comprising the steps of:
   A. generating a plurality of training data sets, each training data set including measurements of flexion-extension bending, lateral bending, and rotational bending associated with an historical occurrence of the low back pain condition, and a known diagnosis value associated with the historical occurrence of the low back pain condition;
   B. training the neural network using the plurality of training data sets; and
   C. generating a target diagnosis value based upon selected measurements of flexion-extension bending, lateral bending, and rotational bending for an unknown low back pain condition.

* * * * *

UNITED STATES PATENT AND TRADEMARK OFFICE
CERTIFICATE OF CORRECTION

PATENT NO. : 6,090,044
DATED : July 18, 2000
INVENTOR(S) : Jeffrey B. Bishop et al.

It is certified that error appears in the above-identified patent and that said Letters Patent is hereby corrected as shown below:

Title page,
Item [56], U.S. PATENT DOCUMENTS, insert
-- 5,455,890   10/1995    Wang ..................... 395/22
   5,463,548   10/1995    Asada et al. .............. 364/413.02
   5,486,999    1/1996    Mebane ................... 364/401
   5,491,627    2/1996    Zhang et al. .............. 364/413.2
   5,839,438   11/1998    Graettinger et al. ........ 128/630
   5,790,761    8/1998    Heseltine et al. .......... 395/222 --.

Column 6,
Line 50, delete the comma after "site".

Column 8,
Line 24, delete "(www," and insert in lieu thereof -- (www), --.
Line 48, delete "14" and insert -- 1-4 --.

Signed and Sealed this

Eighteenth Day of March, 2003

JAMES E. ROGAN
*Director of the United States Patent and Trademark Office*